(12) United States Patent
Matsumoto et al.

(10) Patent No.: US 6,329,498 B1
(45) Date of Patent: Dec. 11, 2001

(54) POLYPEPTIDE TRANSITION METAL SALTS AND METHOD OF ENHANCING ANTI-HIV ACTIVITY OF POLYPEPTIDE

(75) Inventors: Akiyoshi Matsumoto, Hino; Michinori Waki, Higashimurayama, both of (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 09/284,241

(22) PCT Filed: Oct. 15, 1997

(86) PCT No.: PCT/JP97/03711

§ 371 Date: Apr. 14, 1999

§ 102(e) Date: Apr. 14, 1999

(87) PCT Pub. No.: WO98/16555

PCT Pub. Date: Apr. 23, 1998

(30) Foreign Application Priority Data

Oct. 15, 1996 (JP) .................................................... 8-291215

(51) Int. Cl.⁷ .......................... A61K 38/00; A61K 51/00; A61K 49/00
(52) U.S. Cl. ............................ 530/326; 424/1.17; 424/9.2
(58) Field of Search ............................ 530/326; 424/1.17, 424/9.2

(56) References Cited

U.S. PATENT DOCUMENTS

| | | | |
|---|---|---|---|
| 5,449,752 | 9/1995 | Fujii et al. | 530/326 |
| 5,571,892 | 11/1996 | Fujii et al. | 530/326 |
| 5,776,899 | 7/1998 | Matsumoto et al. | 514/14 |

FOREIGN PATENT DOCUMENTS

| | | |
|---|---|---|
| 5-163298 | 6/1993 | (JP) . |
| 8-504837 | 5/1996 | (JP) . |
| 92/04374 | 3/1992 | (WO) . |
| WO 95/10534 | 4/1995 | (WO) . |

OTHER PUBLICATIONS

Hirokazu Tamamura et al., An Anti–HIV peptide, T22, Forms a Highly Active Complex with Zn (II)., Biochem. Biophys. Res. Commun., vol. 229, No. 2, 648–652, Dec., 1995.

T. Murakami, et al., Chemotherapy, vol. 37, pp. 327–334, "Direct Virus Inactivation of Tachyplesin I and Its Isopeptides from Horseshoe Crab Hemocytes", 1991.

M. Morimoto, et al., Chemotherapy, vol. 37, pp. 206–211, "Inhibitory Effect of Tachyplesin on the Proliferation of Human Immunodeficiency Virus in Vitro", 1991.

H. Nakashima, et al., Antimicrobial Agents and Chemotherapy, pp. 1249–1255, "Anti–Human Immunodeficiency Virus Activity of a Novel Synthetic Peptide, T22 ([TYR–5, 12, LYS–7]Polyphemusin II): A Possible Inhibitor of Virus–Cell Fusion", Jun., 1992.

M. Masuda, et al., Biochemical and Biophysical Research Communications, vol. 189, No. 2, pp. 845–850, A Novel Anti–HIV Synthetic Peptide, T–22 ([TYR$^{5,12}$, LYS$^7$]–Polyphemusin II), Dec. 15, 1992.

H. Tamamura, et al., Chem. Pharm. Bull, vol. 41, No. 5, pp. 978–980, "Antimicrobial Activity and Conformation of Tachyplesin I and its Analogs", 1993.

H. Tamamura, et al., Biochemica et Biophysica Acta, vol. 1163, pp. 209–216, "A Comparative Study of the Solution Structures of Tachyplesin I and a Novel Anti–HIV Synthetic Peptide, T22 ([TYR$^{5,12}$, LYS$^7$]–Polyphemusin II), Determined by Nuclear Magnetic Resonance", 1993.

M. Masuda, et al., J. Pharmacobio–Dyn., vol. 15, p. s–90, "Structure–Activity Relationships of Tachyplesin Analogs as Anti–HIV Agent", 1992.

*Primary Examiner*—Hankyel T. Park
(74) *Attorney, Agent, or Firm*—Oblon, Spivak, McClelland, Maier & Neustadt, P.C.

(57) ABSTRACT

The present invention provides a novel salt compound of a polypeptide represented by formula I and a transition metal which has high antiviral activity against human immunodeficiency virus (HIV).

6 Claims, No Drawings

SEQUENCE LISTING

<160> NUMBER OF SEQ ID NOS: 4

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence:peptide

<400> SEQUENCE: 1

Arg Arg Trp Cys Tyr Arg Lys Cys Tyr Lys Gly Tyr Cys Tyr Arg Lys
 1               5                  10                  15

Cys Arg

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence:peptide

<400> SEQUENCE: 2

Arg Trp Cys Tyr Arg Lys Cys Tyr Arg Gly Ile Cys Tyr Arg Lys Cys
 1               5                  10                  15

Arg

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence:peptide

<400> SEQUENCE: 3

Arg Arg Trp Cys Tyr Arg Lys Cys Tyr Arg Gly Ile Cys Tyr Arg Lys
 1               5                  10                  15

Cys Arg

```
<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence:peptide

<400> SEQUENCE: 4

Arg Arg Trp Cys Tyr Arg Lys Cys Tyr Lys Gly Ile Cys Tyr Arg Lys
 1               5                  10                  15

Cys Arg
```

POLYPEPTIDE TRANSITION METAL SALTS AND METHOD OF ENHANCING ANTI-HIV ACTIVITY OF POLYPEPTIDE

FIELD OF THE INVENTION

This invention relates to a transition metal salt of a polypeptide which exhibits a strong affinity to lipopolysaccharides, particularly endotoxins, and moreover the invention relates to a method of enhancing an antiviral activity (for example, an anti-HIV activity) of the polypeptide by which said antiviral activity is expressed stably and strongly by converting said polypeptide to a transition metal salt, and also relates to a pharmaceutical composition or a drug composition for inhibiting a HIV activity, which comprises said transition metal salt of the polypeptide (hereinafter sometimes described as a polypeptide transition metal salt) as an active component.

BACKGROUND OF THE INVENTION

As shown in the publications below, two families of an antimicrobial polypeptide which exhibits an affinity to endotoxins have been isolated from horseshoe crabs.

See, for example, Shigenaga et al., 1990, J. Biol. Chem., 265:21350–21354; Kawano et al., 1990, J. Biol. Chem., 265:15365–15367; Muta et al., 1990, J. Biochem., 108:261–266; Japanese Laid-Open Patent Application No.167230/1990; Japanese Laid-Open Patent Application No.1152987/1990; Japanese Laid-Open Patent Application No.53799/1990; U.S. Pat. No. 5,068,314 (Published Searched Application No.500194/1990); Miyataetal., 1989, J. Biochem., 106:663–668; Akaji et al., 1989, Chem. Pharm. Bull. 37:2661–2664; Tokunaga and Iwanaga, 1989, Taisha (Metabolism), 26:429–439; Shieh et al., 1989, FEBS Lett., 252:121–124; Nakamura et al., 1988, J. Biol. Chem., 263:16709–16713.

One family, a tachyplesin family has been isolated from the Japanese horseshoe crab, Tachypleus. Three tachyplesins, I, II, and III have been identified. Another family, a polyphemusin family has been isolated from the American horseshoe crab, *Limulus polyphemus*. Two polyphemusins, I and II have been identified.

Both families of said tachyplesins and polyphemusins have been found to inhibit growth of both Gram-negative and Gram-positive bacteria at low concentrations as well as fungi, such as *Candida albicans* and form complexes with a bacterial lipopolysaccharide (Shigenaga et al., 1990, J. Biol. Chem., 265:21350–21354; Muta et al., 1990, J. Biochem., 108:261–266).

Also, a polypeptide of the tachyplesin family has been found to exhibit some inhibition activities for virus, such as influenza virus, vesicular stomatitis virus (Murakami et al., 1991, Chemotherapy, 37, 327–334) or human immunodeficiency virus (Morimoto, et al., 1991, Chemotherapy, 37, 206–211).

On the other hand, with respect to the survival of the highly evolved human beings, development of such drugs is extremly longing that are expected to have a prophylactic or therapeutic effect on acquired immune deficiency syndrome (AIDS) caused by infection with human immunodeficiency virus (HIV).

The present inventors have found a series of novel polypeptide which is basically different from the common structure of the polypeptide of horseshoe crabs and exhibits a high antiviral activity against human immunodeficiency virus(HIV) through the studies on the correlation between structural conversion of the polypeptide with endotoxin affinity and the anti-HIV activity, and these results were published in the publications below (Nakashima et al., 1992, Antimicrob. Agents Chemother., 36: 1249–1255; Masuda et al., 1992, Biochem. Biophys. Res. Commun., 189:845–850; Tamamura et al., 1993, Chem. Pharm. Bull., 41:978–980; Tamamura et al., 1993, Biochem. Biophys. Acta, 1163:209–216; Masudaetal., 1992, J. Pharmacobio. Dyn., 15:s-90; U.S. Pat. No. 5,571,892 (International Publication WO 92/04374); U.S. Pat. No. 5,449,752 (Japanese Laid-Open Patent Application No. 163298/1993)).

From results of investigations on structural requirements for expressing an anti-HIV activity of polypeptide based on a basic structure of polypeptide derived from horseshoe crabs, which consists of 16–18 amino acid residues, the present inventors have further provided and filed an improved invention of a novel concept by focusing on minimum essential structure (International Publication WO 95/10534).

According to the aforementioned invention, the structural concept of such lead compound, a polypeptide, which is derived from the polypeptide of the horseshoe crabs as a standard material and exhibits an anti-HIV activity can be summarized into formula [I] below.

$$\underset{A_1}{1} - \underset{a_2}{2} - \underset{Cys}{3} - \underset{A_2}{4} - \underset{A_3}{5} - \underset{A_3}{6} - \underset{X}{7} - \underset{Y}{8} - \underset{Z}{9} - \underset{A_2}{10} - \underset{A_3}{11} - \underset{A_3}{12} - \underset{Cys}{13} - \underset{A_3}{14} - \underset{A_4}{15} \quad \text{[I] (SEQ ID NO: 1)}$$

(wherein $A_1$ independently represents a basic amino acid residue selected from Lys, Arg and Orn; a peptide residue having at least two of said basic amino acid residue; or an N-α substituted amino acid residue or an N-α substituted peptide residue in which a hydrogen atom of N-α position of an amino acid residue in an amino terminus of said basic amino acid residue or said peptide residue may be replaced with an acyl group or a substituted thiocarbamoyl group;

$A_2$ independently represents an amino acid residue selected from Phe, Trp and Tyr;

$A_3$ independently represents a basic amino acid residue selected from Arg, Lys and Orn;

$A_4$ represents an —OH (derived from a carboxyl group) or an —NH$_2$ (derived from an acid amide group);

X represents a peptide residue of two amino acid residues where at the next position of one amino acid residue selected from Ala, Val, Leu, Ile, Ser, Met and Cys, one of the amino acid of $A_2$ is connected via a peptide bond;

Y represents a peptide residue of two amino acid residues which consist of a combination of Gly and one amino acid residue selected from $A_3$, or a peptide residue of two amino acid residues which consist of a combination of Pro and one amino acid residue selected from D-Arg, D-Lys and D-Orn;

Z represents a peptide residue of two amino acid residues where at the next position of one amino acid residue selected from Ala, Val, Leu, Ile, Ser, Met and $A_2$, Cys is connected via a peptide bond;

and X-Y-Z residue connected via peptide bonds is connected to each amino acid residue at the 6th and 10th positions via peptide bonds, or due to the concurrent deletion of X and Z, the residue Y may be connected directly to each amino acid residue at the 6th and 10th positions via peptide bonds, wherein the hydrogen atom of a side chain ω-amino group of D-Lys, L-Lys, D-Orn or L-Orn which is a constituent amino acid of Y may be substituted with ω-aminoacyl group).

It has been disclosed already that the polypeptide having a structure of the above-mentioned formula [I] can be provided in addition to the exhibition of its high anti-HIV activity, can maintain the activity by modification of a specific site without lowering the activity, but rather provide a polypeptide of characteristics by the modification which allows a wide variety of selection of physical and/or chemical properties and therapeutic usage that the basic structure has, for example, to increase or decrease its hydrophilicity or lipophilicity, to selectively accumulate it onto a specific tissue, organ or cell, to increase or decrease its retention time in the body, or to develop dosage forms. Among the polypeptide of the formula [I], polypeptides per se which exhibit high anti-HIV activity are exemplified in Table 1.

why the polypeptide shown in formula [I] specifically shows an anti-HIV activity.

The first object of the present invention is to provide a novel polypeptide transition metal salt which shows an antiviral activity and has a specific structural formula, and the second object is, by converting said polypeptide into a transition metal salt, to provide a method of enhancing physiological activities, especially antiviral activities such as anti-HIV activity and a method of exhibiting pharmaceutically stable activities as a therapeutic agent and to provide a drug composition.

DISCLOSURE OF INVENTION

The present invention relates to a transition metal salt of the polypeptide shown in formula [I] which exhibits a strong affinity to lipopolysaccharides, particularly endotoxins, and the present invention further relates to a method of enhancing antiviral activity (for example, anti-HIV activity) of the polypeptide stably and strongly by converting said polypeptide to a transition metal salt.

TABLE 1

```
Number [I]

1  2  3   4  5  6   7 8 9 10 11 12 13  14 15
      A1-A2-Cys-A2-A3-A3-X-Y-Z-A2-A3-A3-Cys-A3-A4                              (SEQ ID NO: 1)

1    2    3    4    5    6      7      8      9    10   11   12   13   14   15
(1) Arg-Arg-Trp-Cys-Tyr-Arg-Lys-Cys-Tyr-Lys-Gly-Tyr-Cys-Tyr-Arg-Lys-Cys-Arg-NH2   (SEQ ID NO: 2)

1    2    3    4    5    6     (7)     8     (9)    10   11   12   13   14   15
(2) Arg-Arg-Trp-Cys-Tyr-Arg-Lys----------DLys-Pro-----------Tyr-Arg-Lys-Cys-Arg-NH2

(3) Arg-Trp-Cys-Tyr-Arg-Lys-Cys-Tyr-Arg-Gly-Ile-Cys-Tyr-Arg-Lys-Cys-Arg-NH2       (SEQ ID NO: 3)

(4) Arg-Arg-Trp-Cys-Tyr-Arg-Lys-Cys-Tyr-Arg-Gly-Ile-Cys-Tyr-Arg-Lys-Cys-Arg-NH2   (SEQ ID NO: 4)

(5) Ac-Arg-Arg-Trp-Cys-Tyr-Arg-Lys-Cys-Tyr-Arg-Gly-Ile-Cys-Tyr-Arg-Lys-Cys-Arg-NH2 (SEQ ID NO: 4)

(6) Parm-Arg-Arg-Trp-Cys-Tyr-Arg-Lys-Cys-Tyr-Lys-Gly-Ile-Cys-Tyr-Arg-Lys-Cys-Arg-NH2 (SEQ ID NO: 5)

(7) FTC-Arg-Arg-Trp-Cys-Tyr-Arg-Lys-Cys-Tyr-Lys-Gly-Tyr-Cys-Tyr-Arg-Lys-Cys-Arg-NH2 (SEQ ID NO: 2)

1    2    3    4    5    6     (7)    8     (9)   10   11   12   13   14   15
(8) Myr-Arg-Arg-Trp-Cys-Tyr-Arg-Lys-Cys-Tyr-Lys-Gly-Tyr-Cys-Tyr-Arg-Lys-Cys-Arg-NH2 (SEQ ID NO: 2)

(9) Arg-Arg-Trp-Cys-Tyr-Arg-Lys-Cys-Tyr-DLys-Pro-Tyr-Cys-Tyr-Arg-Lys-Cys-Arg-NH2

(10) Arg-Arg-Trp-Cys-Tyr-Arg-Lys-Cys-Tyr-Pro-DLys-Ile-Cys-Tyr-Arg-Arg-Cys-Arg-NH2

(11)                         ε-N-Ac- ─────────┐
                                               │
     Arg-Arg-Trp-Cys-Tyr-Arg-Lys-----------DLys-Pro-----------Tyr-Arg-Lys-Cys-Arg-NH2

(12) FTC-Arg-Arg-Trp-Cys-Tyr-Arg-Lys------------DLys-Pro-----------Tyr-Arg-Lys-Cys-Arg-NH2

(13)                         ε-N-But─────────┐
                                              │
     FTC-Arg-Arg-Trp-Cys-Tyr-Arg-Lys------------DLys-Pro-----------Tyr-Arg-Lys-Cys-Arg-NH2

(14)                             ε-N-Ac-──────────┐
                                                   │
     FTC-Arg-Arg-Trp-Cys-Tyr-Arg-Lys------------Pro-DLys-----------Tyr-Arg-Lys-Cys-Arg-NH2
```

The present inventors accomplished the present invention by obtaining the fact that salt formation between the polypeptide of formula [I] and a transition metal compound allows to exhibit and retain a high anti-HIV activity of the polypeptide stably through a process to elucidate the reason More precisely, the present invention relates to (1) a polypeptide transition metal salt compound which is a salt of a transition metal and a polypeptide shown in the following formula;

```
1    2    3    4    5    6    7   8   9   10   11   12   13    14   15      [I] (SEQ ID NO: 1)
A₁ - A₂ - Cys - A₂ - A₃ - A₃ - X - Y - Z - A₂ - A₃ - A₃ - Cys - A₃ - A₄
```

(wherein $A_1$ independently represents a basic amino acid residue selected from Lys, Arg and Orn; a peptide residue having at least two of said basic amino acid residue; or an N-α substituted amino acid residue or an N-α substituted peptide residue in which a hydrogen atom of N-α position of an amino acid residue in an amino terminus of said basic amino acid residue or said peptide residue may be replaced with an acyl group or a substituted thiocarbamoyl group;

$A_2$ independently represents an amino acid residue selected from Phe, Trp and Tyr;

$A_3$ independently represents a basic amino acid residue selected from Arg, Lys and Orn;

$A_4$ represents an —OH (derived from a carboxyl group) or an —NH₂ (derived from an acid amide group);

X represents a peptide residue of two amino acid residues where at the next position of one amino acid residue selected from Ala, Val, Leu, Ile, Ser, Met and Cys, one of the amino acid of $A_2$ is connected via a peptide bond;

Y represents a peptide residue of two amino acid residues which consist of a combination of Gly and one amino acid residue selected from $A_3$, or a peptide residue of two amino acid residues which consist of a combination of Pro and one amino acid residue selected from D-Arg, D-Lys and D-Orn;

Z represents a peptide residue of two amino acid residues where at the next position of one amino acid residue selected from Ala, Val, Leu, Ile, Ser, Met and $A_2$, Cys is connected via a peptide bond;

and X-Y-Z residue connected via peptide bonds is connected to each amino acid residue at the 6th and 10th positions via peptide bonds, or due to the concurrent deletion of X and Z, the residue Y may be connected directly to each amino acid residue at the 6th and 10th positions via peptide bonds, wherein the hydrogen atom of a side chain ω-amino group of D-Lys, L-Lys, D-Orn or L-Orn which is a constituent amino acid of Y may be substituted with ω-aminoacyl group) or an addition salt of said polypeptide transition metal salt compound and an acid;

(2) the polypeptide transition metal salt compound or the addition salt of said polypeptide transition metal salt compound and an acid according to (1), wherein the salt of transition metal is a complex salt;

(3) the polypeptide transition metal salt compound or the addition salt of said polypeptide transition metal salt compound and an acid according to (1) or (2), wherein the transition metal is selected from the group consisting of an iron group of Fe, Co and Ni, a copper group of Cu, Ag and Au, a zinc group of Zn, Cd and Hg and a manganese group of Mn, Tc and Re;

(4) a method of enhancing and expressing a high and stable anti-HIV activity of the polypeptide compound shown in the following formula;

(wherein $A_1$ independently represents a bas group and the like are exemplifed. As substituents for substituted thiocarbamoyl groups which may be substituted for a hydrogen atom at the aforementioned N-α position, fluorescein group, phenyl group, substituted phenyl group (for example, dimethylaminophenyl azophenyl group and the like) and the like are exemplified.

As ω-aminoacyl groups which may be substituted for a hydrogen atom of the side chain ω-amino group of D-Lys, L-Lys, D-Orn or L-Orn which is a constituent amino acid residue of the aforementioned Y, ω-aminoacyl group having 2 to 6 carbon atoms are exemplified, and specifically ω-aminoacetyl group, ω-aminobutyryl group, ω-aminohexanoyl group and the like are exemplified.

BEST MODE FOR CARRYING OUT THE INVENTION

Definitions

In the polypeptide sequence defined herein, each symbol represents an amino acid residue or a substituted amino acid residue according to the three-letter abbreviation which is internationally accepted, and unless otherwise specified, the amino acid residue or the substituted amino acid residue shows a L-form. For instance, each symbol shows the following amino acid or substituted amino acid.

Ala (alanine); Arg (arginine); Cys (cysteine); Ile (isoleucine); Gly (glycin); Leu (leucine); Ser (serine); Met (methionine); Lys (lysine); Orn (ornithine); Phe (phenylalanine); Pro (proline); Trp (tryptophan); Tyr (tyrosine); Val (valine); DArg (D-arginine); DLys (D-lysine); DOrn (D-ornithine); Ac-Arg (N-α-acetylarginine); FTC-Arg (N-α-fluorescein thiocarbamoyl arginine); Laur-Arg (N-α-lauroyl arginine); Myr-Arg (N-α-myristoyl arginine); Nicot-Arg (N-α-nicotinoyl arginine); Oct-Arg (N-α-octanoyl arginine); Parm-Arg (N-α-palmitoyl arginine); Parm-Orn (N-α-palmitoyl ornithine); PTC-Arg (N-α-phenylthiocarbamoyl arginine); ε-N-Ac-DLys (ε-N-ω-aminoacetyl-D-lysine) and ε-N-But-DLys (ε-N-ω-aminobutyryl-D-lysine).

The present invention have been accomplished by the above-mentioned viewpoints, provides a salt of polypeptide including a salt of a transition metal selected from the group consisting of an iron group, a copper group, a zinc group, and a manganese group and a polypeptide shown in the following formula;

```
1    2    3     4    5    6    7   8   9   10   11   12    13    14   15      [I] (SEQ ID NO: 1)
A₁ - A₂ - Cys - A₂ - A₃ - A₃ - X - Y - Z - A₂ - A₃ - A₃ - Cys - A₃ - A₄
```

(wherein $A_1$ independently represents a basic amino acid residue selected from Lys, Arg and Orn; a peptide residue having at least two of said basic amino acid residue; or an N-α substituted amino acid residue or an N-α substituted peptide residue in which a hydrogen atom of N-α position of an amino acid residue in an amino terminus of said basic amino acid residue or said peptide residue may be replaced with an acyl group or a substituted thiocarbamoyl group;

$A_2$ independently represents an amino acid residue selected from Phe, Trp and Tyr;

$A_3$ independently represents a basic amino acid residue selected from Arg, Lys and Orn;

$A_4$ represents an —OH (derived from a carboxyl group) or an —NH$_2$ (derived from an acid amide group);

X represents a peptide residue of two amino acid residues where at the next position of one amino acid residue selected from Ala, Val, Leu, Ile, Ser, Met and Cys, one of the amino acid of $A_2$ is connected via a peptide bond;

Y represents a peptide residue of two amino acid residues which consist of a combination of Gly and one amino acid residue selected from $A_3$, or a peptide residue of two amino acid residues which consist of a combination of Pro and one amino acid residue selected from D-Arg, D-Lys and D-Orn;

Z represents a peptide residue of two amino acid residues where at the next position of one amino acid residue selected from Ala, Val, Leu, Ile, Ser, Met and $A_2$, Cys is connected via a peptide bond;

and X-Y-Z residue connected via peptide bonds is connected to each amino acid residue at the 6th and 10th positions via peptide bonds, or due to the concurrent deletion of X and Z, the residue Y may be connected directly to each amino acid residue at the 6th and 10th positions via peptide bonds, wherein the hydrogen atom of a side chain ω-amino group of D-Lys, L-Lys, D-Orn or L-Orn which is a constituent amino acid of Y may be substituted with ω-aminoacyl group) and also provides a salt of said polypeptide wherein the salt of transition metal is a complex salt, and the object thereof is, by converting said polypeptide of formula [I] having high anti-HIV activity into a salt product, to provide a method of enhancing the activity of the polypeptide more highly and stably.

A novel polypeptide transition metal salt compound of the present invention will be illustrated in more detail hereinafter.

Preparation of Polypeptides

A polypeptide shown in formula [I] of the present invention can be prepared by known methods per se, for example, solid phase synthetic technique described in "Solid Phase Peptide Synthesis", Stewart & Young, Pierce Chemical Co., Rockford, Ill. (1984). In case of N-α acylamino acid residue or N-α acylpeptide residue where the hydrogen atom at the N-α position of the amino terminal amino acid residue is replaced by an acyl group in $A_1$ of the formula [I], a straight-chain polypeptide of formula [I] is linked to an insoluble resin to prepare a polypeptide resin, said polypeptide resin and an acid anhydride or a carboxylic acid corresponding to an acyl group are allowed to react by using a condensation agent to acylate said N-terminal amino group and to produce an N-acylated polypeptide resin. Then, the insoluble resin and protecting groups of the amino acids are eliminated to prepare a straight-chain polypeptide of the formula [I]. In case of N-α-substituted thiocarbamoyl amino acid residue or N-α-substituted thiocarbamoyl peptide residue where the hydrogen atom at the N-α position of the amino terminal amino acid residue is replaced by a substituted thiocarbamoyl group in $A_1$ of the formula [I], the N-terminal N-α-substituted thiocarbamoyl polypeptide of the present invention can be obtained by reaction of the aforementioned polypeptide with a substituted isothiocyanate compound under slightly alkaline conditions.

In the thus obtained polypeptide, the carboxyl terminus of the amino acid residue at the 14-position can be either free ($A_4$ corresponds to —OH) or converted to an acid amide ($A_4$ corresponds to —NH$_2$).

Unless otherwise indicated, the individual amino acid used in the aforementioned solid phase synthesis method is in the L-form, and the basic amino acid coupled with a proline at the 8th position denoted by Y is limited to D-form.

Alternatively, the polypeptide of the present invention may also be produced using recombinant DNA technology. Accordingly, the nucleotide coding sequences for the polypeptide of the present invention may be cloned and expressed using techniques well known in the art.

See, for example, Maniatis et al., Molecular Cloning, A Laboratory Mannual, Cold Spring Harbor Laboratory, Cold Spring Harbor, N.Y., 1991.

The polypeptide of the present invention can be isolated and purified by means known in the art for polypeptides, for example, extraction, recrystallization, various chromatographies (gel filtration, ion exchange, partition, adsorption, reverse-phase), electrophoresis, counter-current distribution, etc., and reverse-phase high performance liquid chromatography is the most effective.

For specified examples according to such manufacturing methods can be referred as the following specifications; U.S. Pat. No. 5,571,892 (International Publication WO 92/04374); U.S. Pat. No. 5,449,752 (Japanese Laid-Open Patent Application No. 163298/1993) and International Publication WO 95/10534.

The polypeptide shown by formula [I] contains Cys, Arg and Lys residues in the molecule and, according to stereostructural information, at least one pair of Cys residue or Arg residue takes conformation such that —SH side chain or guanidine side chain per se, locates at the same side in the stereostructure, so said side chain is apt to stably form a complex salt with a transition metal compound. However, said polypeptide usually takes an oxidized form of —S—S—, so, it is preferable that said polypeptide should be previously changed to reduced (—SH) form for easier formation of the complex salt with a transition metal.

For example, the transition metal salt can be formed by adding at least two equivalents of transition metal salt, preferably a water soluble salt of a transition metal and an organic or inorganic acid (for example, zinc acetate), to an aqueous neutral solution of said reduced form of polypeptide.

The transition metal salt compound of the polypetide shown in formula [I] of the present invention shows an extremely strong basicity.

Due to this basicity, an addition salt is formed by adding an acid. A salt with a pharmaceutically acceptable acid, for example, an inorganic acid such as hydrochloric acid, hydrobromic acid, phosphoric acid, nitric acid, sulfuric acid and the like, an organic carboxylic acid such as acetic acid, halogenated acetic acid such as trifluoroacetic acid, propionic acid, maleic acid, succinic acid, malic acid, citric acid, tartaric acid, salicylic acid and the like, an acidic sugar such as glucuronic acid, galacturonic acid, gluconic acid, ascorbic acid and the like, an acidic polysaccharide occasionally including polysaccharide sulfates, such as hyaluronic acid, chondroitin sulfates, alginic acid and the like, an organic sulfonic acid such as metanesulfonic acid, p-toluenesulfonic acid and the like is formed. The transition metal salt with the polypeptides shown in formula [I] of the present invention can be used for preparing a drug composition as an addition salt with said pharmaceutically acceptable acid.

Usages of the Present Polypeptide Transition Metal Salt Compound

The transition metal salt compound of the polypeptide shown in formula [I] has an ability to bind to endotoxins, an antibacterial activities, and an activity to hemolyze endotoxin-sensitized hemocytes. In addition, the polypeptide transition metal salt compound of the present invention possesses extremely high antiviral activities. In a specific embodiment, the polypeptide transition metal salt compound of the present invention has an anti-HIV activity. A medicine, especially an anti-HIV agent, by the present invention can be prepared as a medicine composition comprising the transition metal salt compound of the polypeptide shown in formula [I] or an addition salt of said transition metal salt compound with a pharmaceutically acceptable acid as effective component and a pharmaceutically acceptable carrier selected in accordance with the administration method and administration form. As the pharmaceutical carriers, physiologically compatible buffers such as Hank's or Ringer's solution, physiological saline, a glucose physiological saline or a mixture thereof, and heparinized citric acid-sodium-citrate-dextrose solution are exemplified. The anti-HIV agent of the present invention is orally or parenterally administered in accordance with the object of treatment, or disinfection of a virus disease within the body or virus-infected portions outside of the body such as the surface of the body and can be prepared as a preparation such as powder, granules, a solution for injection or oral administration, tablets, suppositories, pessaries, ointment, cream or aerosol, using appropriate pharmaceutical carriers in accordance with the administration method.

When the anti-HIV agent of the present invention is directly administered as an injection to a patient, the polypeptide or its salt of the present invention is dissolved in physiological saline and administered continuously or intermittently in an amount of 10 to 5,000 mg per kg of human body weight and per one day and by intravenous drip.

EXAMPLES

The present invention is further embodied in the examples shown below which are not intended to limit the invention.

In the examples herein, the preparation examples of transition metal salts of polypeptide (1) and polypeptide (2), are described, and the test results of anti-HIV activity assays for the polypeptide transition metal salts of the invention and known polypeptides with endotoxin-affinity are disclosed.

Example 1

Preparation of a Polypeptide (1) Zinc Complex Salt

The following polypeptide (1) was synthesized and provided using the method described in U.S. Pat. No. 5,571,892 (International Publication WO92/04374) and U.S. Pat. No. 5,449,752 (Japanese Laid-Open Patent Application No. 163298/1993).

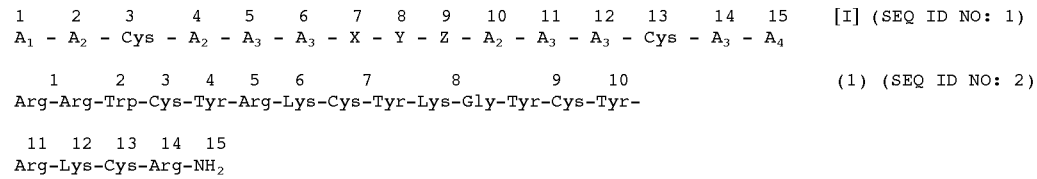

1.1 Preparation of a Reduced form of the Polypeptide (1)

The polypeptide (1) acetate (10.2 mg, 3.37 μmol) prepared according to the aforementioned PCT International Publication was dissolved in purified water (0.5 ml). To this solution, dithiothreitol (manufactured by Seikagaku Corporation) (26.0 mg, 169 μmol) of 50 times equivalent to the polypeptide (1) was added, flushed with nitrogen gas, and stirred under nitrogen stream at room temperature for two hours. The process of said reduction reaction was traced with HPLC to confirm the complete progress of reduction.

Said reaction solution after completion of the reduction reaction was applied to a Sephadex G-25 (fine) (Pharmacia Biotech Co., Ltd.) column (2.5×70 cm) which has previously equilibrated with an aqueous solution of 25% acetic acid, eluted with the same aqueous solution of 25% acetic acid and then fractionated (1 fraction=224 drops). Fractional portions of fraction numbers 26 and 27 which were shown to be positive in the Ellman reaction (G. L.Ellman, Arch. Biochem. Biophys., 82, 70 (1959); detection method for thiol groups) and fluorescamine reaction (A. M.Felix et al., J. Chromatogr., 89, 361 (1974); fluorescence detection method of amino groups) were collected and said fraction solution was concentrated in vacuo, and after dilution with an aqueous solution of 10% acetic acid, the solution was lyophilized to obtain desired acetate of the reduced form of the polypeptide (1) of interest.

Yield: 6.8 mg (67%)

1.2 Analysis of the Reduced form of the Polypeptide (1)

The acetate of the reduced form of the polypeptide (1) obtained in 1.1 was acid-hydrolysed in 4 M methanesulfonic acid containing 0.2% tryptamine at 115° C. for 24 hours according to the method of Liu et al (T.-Y. Liu et al., J. Biol. Chem., 251, 1936 (1976)). The amino acid composition thereof was well consistent with the amino acid composition of the reduced form of the polypeptide (1).

Specific optical rotation $[\alpha]^{20}D$ of the resulting acetate of the reduced form of the polypeptide (1) was −26.0° (c=0.09, an aqueous solution of 1M acetic acid).

Moreover, the resulting acetate of the reduced form of the polypeptide (1) showed a single peak in HPLC analysis under the following conditions.

Conditions for HPLC Analysis and the Results

Column: TSK gel ODS–120 T (0.46×15 cm) (Toso Co., Ltd.)+TSK gurd gel ODS–120 T (0.32×1.5 cm) (Toso Co., Ltd.)

Gradient elution:

Eluents:
  10% acetonitrile/0.1% trifluoroacetic acid (A solution)
  80% acetonitrile/0.1% trifluoroacetic acid (B solution)

Gradient conditions:

| Gradient time | Concentration of B solution | Concentration of A solution |
|---|---|---|
| 1.0 min | 0% | 10% |
| 29.4 min | 42% | 39.4% |
| 35.0 min | 100% | 80% |

Temperature: 40° C.
Flow rate: 0.8 ml/min
Detection: 220 nm and 280 nm
Amount applied: 5 μl
(peptide concentration: 1 mg/ml)

| Elution time: | |
|---|---|
| acetate of reduced form of polypeptide (1) | 19.27 min |
| acetate of polypeptide (1) | 18.24 min |

1.3 Preparation of a Complex Salt of the Reduced form of the Polypeptide (1) and Zinc (II) Ion The acetate of the reduced form of the polypeptide (1) obtained in 1.1 was dissolved into purified water or 1 M ammonium acetate butter solution (pH 7.2).

To this aqueous solution or buffer solution, an aqueous solution of 0.005 M zinc acetate corresponding to two equivalent zinc (II) ion to the reduced form of the polypeptide (1) was added. The final concentration of the polypeptide was adjusted to be 5 mg/ml to obtain a complex solution of the reduced form of the polypeptide (1) and zinc (II) ion.

1.4 Confirmation of Structure of the Complex Salt of the Reduced form of the Polypeptide (1) and Zinc (II) Ion by Ion Spray Mass Spectrometry A portion of the complex solution of the reduced form of the polypeptide (1) and zinc (II) ion obtained in 1.3 was taken out, and the solution was used as a subject solution for structural analysis and the structural analysis was conducted by ion spray mass spectrometry under the following conditions.

Conditions for Ion Spray mass Spectrometry

Equipment: triple stage quadrupole mass spectrometer AP IIIE type (manufactured by Perkin—Elmer Sciex Co., Ltd.; serviced by Takara Shuzo Co., Ltd.)

Sample infusion: Harvard Apparatus syringe infusion pump 22 (South Natick, Mass.) is used to infuse at a flow rate of 5 μl/min Orifice voltage: 130 V Mass spectra region and the like: the mass vs. electric charge (m/z) 600–1800

(in the positive ion-mode at a stepwise of 0.5 amu, on average of 30 scans)

Analysis of the obtained data: analyzed by Macspec 3.22 (Sciex)

Results of Ion Spray Mass Spectrometry

Mass values for the charge states of 2+ and 3+ (m/z: 1277.00 and 851.67) were observed, respectively, and the reconstructed mass value (m/z: 2552.48) was well consistent with the calculated mass value for the reduced polypeptide (1)+Zn−4H (m/z: 2552.40).

In other words, it is shown that the reduced polypeptide (1) and zinc (II) ion form a complex wherein peptide:Zn= 1:1.

Considerations

It has already reported that the structure of a complex consisting of a peptide or protein and a metal can be identified by ion spray mass spectrometry or electro spray mass spectrometry. For example, see analysis of zinc finger structure of a DNA binding domain of glucocorticoid receptor by H. E. Witkowska et al. (J. Amer. Chem. Soc., 117, 3319 (1995)), analysis of coordination structure of copper to zinc finger protein domain by T. W. Hutchens et al. (FEBS Lett., 309, 170 (1992)), and the review by Umeda on ion spray mass spectrometry (Tanpakushitsu Kakusan Koso, 36, 1655 (1991)) and the like.

Also in this experiment, it was found that the structure of the complex of the reduced form of the polypeptide (1) and zinc (II) ion can be identified by ion spray mass spectrometry.

1.5 Confirmation of the Structure of the Complex Salt of the Reduced form of the Polypeptide (1) and Zinc (II) Ion by Ultraviolet Absorption Spectrophotometry Portions of the aqueous solution of the reduced form of the polypeptide (1) obtained in 1.1 and the complex solution of the reduced form of the polypeptide (1) and zinc (II) ion obtained in 1.3 were taken out, and each solution was used as a subject solution for structural analysis and the structural analysis was conducted by measuring ultraviolet absorption spectra and their difference spectra under the following conditions.

Measurements of Ultraviolet Absorption Spectra
  Equipment: Ultraviolet-visible spectrophotometer Ubest—30 (Nihon-Bunko Co., Ltd.)
  Measured wavelength: 200–340 nm
  Sample: After placing each subject which was fleshly prepared into a measurement tube, it was flushed with nitrogen gas and immediately measured
  Regular ultraviolet absorption spectra:
    Control side: distilled water
    Subject side: the solution of the reduced form of the polypeptide (1) and the complex solution of the reduced form of the polypeptide (1) and zinc (II) ion
  Ultraviolet difference spectra:
    Control side: the solution of the reduced form of the polypeptide (1)
    Subject side: the complex solution of the reduced form of the polypeptide (1) and zinc (II) ion Results of the Measurements of Ultraviolet Absorption Spectra
  Regular ultraviolet absorption spectra:
    The solution of the reduced form of the polypeptide (1): A large absorption peak was shown at 250–300 nm which is a characterized absorption for Trp of a constituent amino acid of the polypeptide (1). The absorption maximum at 278 nm and a shoulder at 280 nm were shown which are characteristic absorptions due to Trp.
    Complex solution of the reduced form of the polypeptide (1) and zinc (II) ion: An absorption curve which was broadly added to the absorption curve of the aforementioned reduced form of the polypeptide (1) solution ranging from the proximity of 250 nm to 200 nm was obtained. To further clarify the absorption wavelength, the following difference spectrum was measured.
  Ultraviolet difference spectrum:
    A difference spectrum having its peak ranging from 215–235 nm as its deference absorption was obtained.

Analysis of the Resulting Ultraviolet Absorption Spectra
  As shown above, when adding zinc (II) ion to the reduced form of the polypeptide (1) solution, it was observed that the ultraviolet absorption broadly expands mainly in the range of 215–235 nm.
  This observation result implicates, as considered later, that in the solution of the reduced form of the polypeptide (1) and zinc (II) ion, the SH group of Cys of the reduced form of the polypeptide (1) forms a complex with zinc (II) ion through a mercaptide bond.

Considerations
  It is known that methallothionein, a protein which relates to heavy metal detoxification, has a structure where the SH group of the constituent Cys residue forms a complex with cadmium (II), zinc (II), copper (I, II), mercury (II) ion or the like through a mercaptide bond, and when a metal binds to an apo-metallothionein (the SH form), the ultraviolet absorption is increased within the range of wavelength characteristic of each metal mercaptide bond. For example, in the case of a mercaptide bonding complex with zinc (II) ion, the ultraviolet absorption is known to be broadly increased mainly within the range of 220–230 nm (see, J. H. R. Kagi and B. L. Vallee, J. Biol. Chem., 236, 2435 (1961); M. Vasak et al., Biochemistry, 20, 2852 (1981); A. R. Thrower et al., J. Biol. Chem., 263, 7037 (1988); J. H. R. Kagi et al., Environmental Health Perspectives, 54, 93 (1984), and the like). The broad range where the ultraviolet absorption increases (220–230 nm) due to the mercaptide bond of this zinc (II) ion is consistent with the increased wavelength range of the difference spectrum observed in the above solution of the reduced form of the polypeptide (1) and zinc (II) ion.
  In other words, it is clarified that in the solution of the reduced form of the polypeptide (1) and zinc (II) ion, the SH group of Cys of the reduced form of the polypeptide (1) forms a mercaptide bond with zinc (II) ion.

1.6 Anti-HIV Activity of the Complex Salt of the Reduced form of the Polypeptide (1) and Zinc (II) Ion
  A portion of the complex solution of the reduced form of the polypeptide (1) and zinc (II) ion obtained in 1.3 was taken out, and the solution was used as a subject solution for measurement of anti-HIV activity and the anti-HIV activity was measured.

Example 2

Preparation of a Polypeptide (2) Zinc Complex Salt

The polypeptide (2) as shown in the following formula was prepared and provided according to the method described in PCT International Publication WO 95/10534.

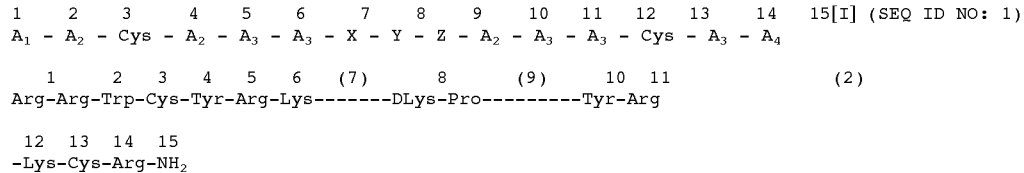

```
   1    2    3    4    5    6    7   8   9   10   11   12   13   14   15[I]  (SEQ ID NO: 1)
   A₁ - A₂ - Cys - A₂ - A₃ - A₃ - X - Y - Z - A₂ - A₃ - A₃ - Cys - A₃ - A₄

1   2   3   4   5   6  (7)    8    (9)    10  11              (2)
   Arg-Arg-Trp-Cys-Tyr-Arg-Lys-------DLys-Pro---------Tyr-Arg 12  13  14  15
   -Lys-Cys-Arg-NH₂
```

2.1. Preparation of a Reduced form of the Polypeptide (2)
  Acetate of the polypeptide (2) (10.0 mg, 3.94 μmol) prepared according to the aforementioned PCT International Publication was dissolved into purified water (0.5 ml). To this solution, dithiothreitol (32.0 mg, 207.5 μmol) (manufactured by Seikagaku Corporation) of 53 times equivalent to the polypeptide (2) was added, flushed with nitrogen gas and stirred under nitrogen stream at room temperature for two hours.
  The progress of said reduction reaction was traced with HPLC and the complete processing of the reduction was confirmed.
  After the completion of the reduction reaction, said reaction solution was applied to a Sephadex G-25 (fine) (Pharmacia Biotech Co., Ltd.) column (2.5×70 cm) which has so previously equilibrated with an aqueous solution of 25% acetic acid, eluted with the same aqueous solution of 25% acetic acid and then fractionated (1 fraction=224 drops). Fractional portions of fraction numbers 25–27 which were shown to be positive in Ellman reaction and fluorescamine reaction were collected and said fraction solution was concentrated in vacuo, and after dilution with an aqueous solution of 10% acetic acid, the solution was lyophilized to obtain the acetate of the reduced form of the polypeptide (2) of interest.

Yield: 9.8 mg (98%)

2.2 Analysis of the Reduced form of the Polypeptide (2)

The acetate of the reduced form of the polypeptide (2) obtained in 2.1 was acid-hydrolyzed in 4 M methanesulfonic acid containing 0.2% tryptamine at 115° C. for 24 hours according to the method of Liu et al. in the same manner as in the polypeptide (1) of 1.2. The amino acid composition thereof was well consistent with that of the reduced form of the polypeptide (2).

Specific optical rotation $[\alpha]^{20}D$ of the resulting acetate of the reduced form of the polypeptide (1) was −23.3° (c=0.04, an aqueous solution of 1M acetic acid).

Moreover, the resulting acetate of the reduced form of the polypeptide (2) showed a single peak in HPLC analysis under the same conditions as those of the HPLC analysis for the polypeptide (1) in 1.2.

| Results from HPLC analysis | |
|---|---|
| Elution time: | |
| acetate of reduced form of polypeptide (2) | 16.14 min |
| acetate of polypeptide (2) | 15.87 min |

2.3 Preparation of a Complex Salt of the Reduced form of the Polypeptide (2) and Zinc (II) Ion The acetate of the reduced form of the polypeptide (2) obtained in 2.1 was dissolved into pulyfied water or 1 M ammonium acetate buffer solution (pH 7.2).

To this aqueous solution or buffer solution, an aqueous solution of 0.005 M zinc acetate corresponding to one equivalent zinc (II) ion to the reduced form of the polypeptide (2) was added. The final concentration of the polypeptide was adjusted to be 5 mg/ml to obtain a complex solution of the reduced form of the polypeptide (2) and zinc (II) ion.

2.4 Confirmation of the Structure of the Complex Salt of the Reduced form of the Polypeptide (2) and Zinc (II) Ion by Ion Spray Mass Spectrometry A portion of the complex solution of the reduced form of the polypeptide (2) and zinc (II) ion obtained in 2.3 was taken out, and the solution was used as a subject solution for structural analysis and the structural analysis was conducted by ion spray mass spectrometry under the same conditions as those for the ion spray mass spectrometry of the complex solution of the reduced form of the polypeptide (1) and zinc (II) ion in 1.4.

Results of Ion Spray Mass Spectrometry

Mass values for the charge states of 2+ and 3+ (m/z: 1030.50 and 687.34) were observed, respectively, and the reconstructed mass value (m/z: 2059.98) was well consistent with the calculated mass value for the reduced polypeptide (2)+Zn−4H (m/z: 2059.83).

In other words, it is shown that the reduced polypeptide (2) and zinc (II) ion form a complex wherein peptide:Zn= 1:1.

2.5 Confirmation of the Structure of the Complex Salt of the Reduced form of the Polypeptide (2) and Zinc (II) Ion by Ultraviolet Absorption Spectrophotometry Portions of the solution of the reduced form of the polypeptide (2) obtained in 2.1 and the complex solution of the reduced form of the polypeptide (2) and zinc (II) ion obtained in 2.3 were taken out, and each solution was used as a subject solution for structural analysis and the structural analysis was conducted by measuring ultraviolet absorption spectra and their difference spectra under the same conditions as those for polypeptide (1) in 1.5.

Measurements of Ultraviolet Absorption Spectra

Regular ultraviolet absorption spectra;

Control side: distilled water

Subject side: the solution of the reduced form of the polypeptide (2) and the solution of the complex salt of the reduced form of the polypeptide (2) and zinc (II)ion.

Ultraviolet Difference Spectra:

Control side: the solution of the reduced form of the polypeptide (2)

Subject side: the complex solution of the reduced form of the polypeptide (2) and zinc (II) ion.

Results of the Measurements of Ultraviolet Absorption Spectra

Regular ultraviolet absorption spectra:

The solution of the reduced form of the polypeptide (2) solution: A large absorption peak was shown at 250–300 nm which is a characterized absorption for Trp of a constituent amino acid of polypeptide (2). The absorption maximum at 278 nm and a shoulder at 280 nm were shown which are characteristic absorptions due to Trp.

Complex solution of the reduced form of the polypeptide (2) and zinc (II) ion: An absorption curve which was broadly added to the absorption curve of the aforementioned reduced form of the polypeptide (2) solution ranging from the proximity of 250 nm to 200 nm was obtained.

Ultraviolet difference spectrum:

A difference spectrum having its peak ranging from 215–235 nm as its difference absorption was obtained.

Analysis of the Resulting Ultraviolet Absorption Spectrum

As shown above, when adding zinc (II) ion to the reduced form of the polypeptide (2) solution, it was observed that the ultraviolet absorption broadly expands mainly in the range of 215–235 nm.

Accordingly, it is shown that in the solution of the reduced form of the polypeptide (2) and zinc (II) ion, the SH group of Cys of the reduced form of the polypeptide (2) forms a complex with zinc (II) ion through a mercaptide bond.

2.6 Anti-HIV Activity of the Complex Salt of the Reduced form of the Polypeptide (2) and Zinc (II) Ion A portion of the complex solution of the reduced form of the polypeptide (2) and zinc (II) ion obtained above was taken out, and the solution was used as a subject solution for measurement of anti-HIV activity and the anti-HIV activity was measured.

Example 3

Antiviral Activity Against Human Immunodeficiency Virus (HIV)

Antiviral activities against HIV of the polypeptide (1) zinc complex prepared according to Example 1 and the polypeptide (2) zinc complex prepared according to Example 2 were tested and estimated according to the following method.

To a 96-well microtiter plate, HIV-infected MT-4 cells ($2.5 \times 10^4$ cells/well, Multiplicity of infection (MOI): 0.001) was added immediately after the infection along with test materials in various concentrations. After incubation in a $CO_2$ incubator at 37° C. for 5 days, survivor cells were measured by the MTT method (Pauwels et al.; J. Virol. Methods 20, 309–321 (1988)). Antiviral activity is expressed as a concentration to suppress 50% of cell death due to HIV infection ($EC_{50}$: 50% effective concentration). On the other hand, in order to know the cytotoxicity of the test substances on the MT-4 cells, virus-non-infected cells were cultured with the test materials in various concentrations as described above. The cytotoxicity is expressed as a 50% cytotoxic concentration ($CC_{50}$: 50% cytotoxic concentration) due to the test materials. And the rough ratio of $CC_{50}$ to $EC_{50}$ ($CC_{50}/EC_{50}$) is expressed as an effective ratio (SI).

The results of the anti-HIV activity measurements are shown in Table 2 along with the results of other compounds.

TABLE 2

Anit-HIV activities of various compounds

| Compound | $CC_{50}$ (µg/ml) | $EC_{50}$ (µg/ml) | SI ($CC_{50}/ED_{50}$) |
|---|---|---|---|
| Polypeptide (1) | 41.53 | 0.0047 | 8928 |
| Polypeptide (1) +$Zn^{++}$ (2 eq) | 38.66 | 0.008 | 4808 |
| Reduced form of polypeptide (1) | 41.27 | 0.0052 | 8011 |
| (Polypeptide (1)/ 2 eq $ZN^{++}$) complex salt | 40.63 | 0.0013 | 30683 |
| Polypeptide (2) | 44.60 | 0.029 | 1565 |
| Polypeptide (2) +$Zn^{++}$ (1 eq) | 38.93 | 0.033 | 1172 |
| Reduced form of (Polypeptide (2)/ 1 eq $Zn^{++}$) complex salt | 41.17 | 0.040 | 1034 |
|  | 54.63 | 0.014 | 4052 |
| $Zn^{++}$ (µM) | 0.48 | 0.15 | 3 |
| Dextran sulfate | >1000 | 0.68 | >1480 |
| AZT (µM) | 1.93 | 0.0011 | 1716 |

---

What is claimed is:

1. A polypeptide transition metal salt compound which is a salt of a transition metal and a polypeptide shown in the following formula;

$$\text{(I) (SEQ ID NO: 1)}$$
$$\begin{array}{cccccccccccccccc}1&2&3&4&5&6&7&8&9&10&11&12&13&14&15\end{array}$$
$$A_1-A_2-Cys-A_2-Cys-A_3-A_3-X-Y-Z-A_2-A_3-A_3Cys-A_3-A_4$$

wherein $A_1$ independently represents a basic amino acid residue selected from Lys, Arg and Orn; a peptide residue having at least two of said basic amino acid residue; or an N-α substituted amino acid residue or an N-α substituted peptide residue in which a hydrogen atom of N-α position of an amino acid residue in an amino terminus of said basic amino acid residue or said peptide residue may be replaced with an acyl group or a substituted thiocarbamoyl group;

$A_2$ independently represents an amino acid residue selected from Phe, Trp and Tyr;

$A_3$ independently represents a basic amino acid residue selected from Arg, Lys and Orn;

$A_4$ represents an —OH which is derived from a carboxyl group or an —NH$_2$ which is derived from an acid amide group;

X represents a peptide residue of two amino acid residues where at the next position of one amino acid residue selected from Ala, Val, Leu, Ile, Ser, Met and Cys, one of the amino acid of $A_2$ is connected via peptide bond;

Y represents a peptide residue of two amino acid residues which consist of a combination of Gly and one amino acid residue selected from $A_3$, or a peptide residue of two amino acid residues which consist of a combination of Pro and one amino acid residue selected from D-Arg, D-Lys and D-Orn;

Z represents a peptide residue of two amino acid residues where at the next position of one amino acid residue selected from Ala, Val Leu, Ile, Ser, Met and $A_2$, Cys is connected via a peptide bond;

and X-Y-Z residue connected via peptide bonds is connected to each amino acid residue at the 6th and 10th positions via peptide bonds, or due to the concurrent deletion of X and Z, the residue Y may be connected directly to each amino acid residue at the 6th and 10th positions via peptide bonds, wherein the hydrogen atom of a side chain ω-amino group of D-Lys, L-Lys, D-Orn or L-Orn which is a constituent amino acid of Y may be substituted with ω-aminoacyl group; or an addition salt of said polypeptide transition metal salt compound and an acid.

2. The polypeptide transition metal salt compound or the addition salt of said polypeptide transition metal salt compound and an acid according to claim 1, wherein the salt of transition metal is a complex salt.

3. The polypeptide transition metal salt compound or the addition salt of said polypeptide transition metal salt compound and an acid according to claim 1, wherein the transition metal is selected from the group consisting of an iron group of Fe, Co and Ni, a copper group of Cu, Ag and Au, a zinc group of Zn, Cd and Hg and a manganese group of Mn, Tc and Re.

4. A pharmaceutical composition or a drug composition comprising an effective amount of the polypeptide transition metal salt compound or the addition salt of said polypeptide transition metal salt compound and an acid according to claim 1 and a pharmaceutical carrier.

5. A composition according to claim 4 to inhibit HIV activities within a patient's body.

6. A method of enhancing anti-HIV activity of the polypeptide compound shown in the following formula;

$$\text{(I) (SEQ ID NO: 1)}$$
$$\begin{array}{cccccccccccccccc}1&2&3&4&5&6&7&8&9&10&11&12&13&14&15\end{array}$$
$$A_1-A_2-Cys-A_2-Cys-A_3-A_3-X-Y-Z-A_2-A_3-A_3Cys-A_3-A_4$$

wherein $A_1$ independently represents a basic amino acid residue selected from Lys, Arg and Orn; a peptide residue having at least two of said basic amino acid residue; or an N-α substituted amino acid residue or an N-α substituted peptide residue in which a hydrogen atom of N-α position of an amino acid residue in an amino terminus of said basic amino acid residue or said peptide residue may be replaced with an acyl group or a substituted thiocarbamoyl group;

$A_2$ independently represents an amino acid residue selected from Phe, Trp and Tyr;

$A_3$ independently represents a basic amino acid residue selected from Arg, Lys and Orn;

$A_4$ represents an OH which is derived from a carboxyl group or an —NH$_2$ which is derived from an acid amide group;

X represents a peptide residue of two amino acid residues where at the next position of one amino acid residue selected from Ala, Val, Leu, Ile, Ser, Met and Cys, one of the amino acid of $A_2$ is connected via a peptide bond;

Y represents a peptide residue of two amino acid residues which consist of a combination of Gly and one amino acid residue selected from $A_3$, or a peptide residue of two amino acid residues which consist of a combination of Pro and one amino acid residue selected from D-Arg, D-Lys and D-Orn;

Z represents a peptide residue of two amino acid residues where at the next position of one amino acid residue selected from Ala, Val, Leu, Ile, Ser, Met and $A_2$, Cys is connected via a peptide bond;

and X-Y-Z residue connected via peptide bonds is connected to each amino acid residue at the 6th and 10th positions via peptide bonds, or due to the concurrent deletion of X and Z, the residue Y may be connected directly to each amino acid residue at the 6th and 10th positions via peptide bonds, wherein the hydrogen atom of a side chain ω-amino group of D-Lys, L-Lys, D-Orn or L-orn which is a constituent amino acid of Y may be substituted with ω-aminoacyl group which comprises converting said polypeptide (I) to a salt with transition metal.

* * * * *